(12) United States Patent
Han et al.

(10) Patent No.: US 11,708,637 B2
(45) Date of Patent: Jul. 25, 2023

(54) METHODS OF SUPPORTING A GRAPHENE SHEET DISPOSED ON A FRAME SUPPORT

(71) Applicants: Bong-Gyoon Han, Castro Valley, CA (US); Robert M. Glaeser, Berkeley, CA (US)

(72) Inventors: Bong-Gyoon Han, Castro Valley, CA (US); Robert M. Glaeser, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/987,173

(22) Filed: Aug. 6, 2020

(65) Prior Publication Data

US 2021/0047740 A1 Feb. 18, 2021
US 2023/0012465 A9 Jan. 12, 2023

Related U.S. Application Data

(60) Provisional application No. 62/886,255, filed on Aug. 13, 2019.

(51) Int. Cl.
*C23F 1/18* (2006.01)
*H01J 37/20* (2006.01)
(Continued)

(52) U.S. Cl.
CPC ............... *C23F 1/18* (2013.01); *A61K 9/19* (2013.01); *A61K 9/5169* (2013.01); *A61P 35/00* (2018.01); *C01B 32/194* (2017.08); *C07H 19/10* (2013.01); *C23F 1/08* (2013.01); *H01J 37/20* (2013.01); *C01B 2204/02* (2013.01); *C01B 2204/04* (2013.01); *H01J 2235/183* (2013.01); *H01J 2237/20* (2013.01); *H01J 2237/26* (2013.01)

(58) Field of Classification Search
CPC . C23F 1/08; C23F 1/18; C01B 32/194; C01B 2204/02; C01B 2204/04
See application file for complete search history.

(56) References Cited

U.S. PATENT DOCUMENTS

2017/0032962 A1* 2/2017 Zurutuza Elorza ......................... H01L 21/02527

FOREIGN PATENT DOCUMENTS

TW 1520901 B * 2/2016 ............ C01B 32/04

OTHER PUBLICATIONS

Güneş, Fethullah, et al. "Large-area graphene-based flexible transparent conducting films." Nano 4.02 (2009): 83-90.*
(Continued)

*Primary Examiner* — Richard M Rump

(57) ABSTRACT

This disclosure provides systems, methods, and apparatus related to graphene. In one aspect, a method includes submerging a frame support in an etching solution that is contained in a container. A growth substrate, a graphene sheet disposed on the growth substrate, and a primary support disposed on the graphene sheet is placed on a surface of the etching solution. The growth substrate is dissolved in the etching solution to leave the graphene sheet and the primary support floating on a surface of the etching solution. The etching solution in the container is replaced with a washing solution. The washing solution is removed from the container so that the graphene sheet becomes disposed on the frame support.

19 Claims, 6 Drawing Sheets

(51) Int. Cl.
*C01B 32/194* (2017.01)
*C23F 1/08* (2006.01)
*A61P 35/00* (2006.01)
*A61K 9/19* (2006.01)
*A61K 9/51* (2006.01)
*C07H 19/10* (2006.01)

(56) References Cited

OTHER PUBLICATIONS

Lee, Yong Bok, Heejun Jang, and Chi Won Ahn. "Formvar Assisted Graphene Transfer for Graphene TEM Grid." Journal of nanoscience and nanotechnology 16.2 (2016): 1810-1813.*
English machine translation of TW1520901B (2016).*

* cited by examiner

METHODS OF SUPPORTING A GRAPHENE SHEET DISPOSED ON A FRAME SUPPORT

RELATED APPLICATIONS

This application claims priority to U.S. Provisional Patent Application No. 62/886,055, filed Aug. 13, 2019, which is herein incorporated by reference.

STATEMENT OF GOVERNMENT SUPPORT

This invention was made with government support under Contract No. DE-AC02-05CH11231 awarded by the U.S. Department of Energy and under Grant No. 2P01GM051487-20A1 awarded by the National Institutes of Health. The government has certain rights in this invention.

TECHNICAL FIELD

This disclosure relates generally to graphene.

BACKGROUND

One currently used graphene-transfer method employs a primary support comprising a continuous polymer film (e.g., polymethyl mecracylate (PMMA)). In order to produce either electron-transparent support films or wet-cell windows, the primary support is removed after the transfer of graphene to a secondary support (also referred to as a grid or a frame) is complete. One problem with this method is that it invariably leaves a contaminating residue on the graphene from the continuous polymer film.

A less commonly used method employs a patterned support that is already attached to a secondary support (e.g., an electron microscope (EM) specimen grid). The patterned support is adhered to the graphene while the graphene is disposed on its original substrate. One problem with this method is that the secondary support is usually not flexible enough to allow the graphene to adhere uniformly over the entire area of the secondary support. As a result, the graphene can wrinkle, fold, and/or rupture on some of the area of the secondary support.

SUMMARY

Described herein are methods of transferring a graphene sheet from a substrate on which the graphene sheet was grown to a secondary substrate or frame on which the graphene sheet is used directly or is subjected to further processing before use. The method uses a primary support comprising a pre-patterned, holey film to transfer the graphene sheet from the substrate on which the graphene sheet was grown. One purpose of this primary support is to reduce or eliminate wrinkling, folding, rupturing, and other mechanical damage to the graphene sheet during transfer and use. At the same time, open areas in the primary support provide regions over which the graphene sheet remains pristine and clean. The open areas in the primary support are holes in the primary support, the holes being defined by size, distribution, and geometry. Such supported graphene films can be used, for example, as electron-transparent specimen substrates and as windows in liquid cells for applications in electron microscopy.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

The terms "about" or "approximate" and the like are synonymous and are used to indicate that the value modified by the term has an understood range associated with it, where the range can be ±20%, ±15%, ±10%, ±5%, or ±1%. The terms "substantially" and the like are used to indicate that a value is close to a targeted value, where close can mean, for example, the value is within 80% of the targeted value, within 85% of the targeted value, within 90% of the targeted value, within 95% of the targeted value, or within 99% of the targeted value.

Embodiments described herein overcome the problems described above with some graphene-transfer methods. The embodiments described herein do not leave contamination on a graphene sheet from a continuous polymer film or reduce or eliminate wrinkling, folding, or rupturing in the graphene sheet due to the secondary support not being flexible.

Embodiments described herein employ a pre-patterned, holey film as a primary mechanical support to transfer a graphene sheet from the substrate on which it was grown to a secondary substrate or frame. The graphene sheet disposed on the secondary substrate can be used for its intended purpose or subjected to further processing before use. For example, the graphene sheet on the secondary substrate can be used as an electron-transparent specimen substrate, as windows in a liquid cell, or for further applications in electron microscopy.

Figure 1:
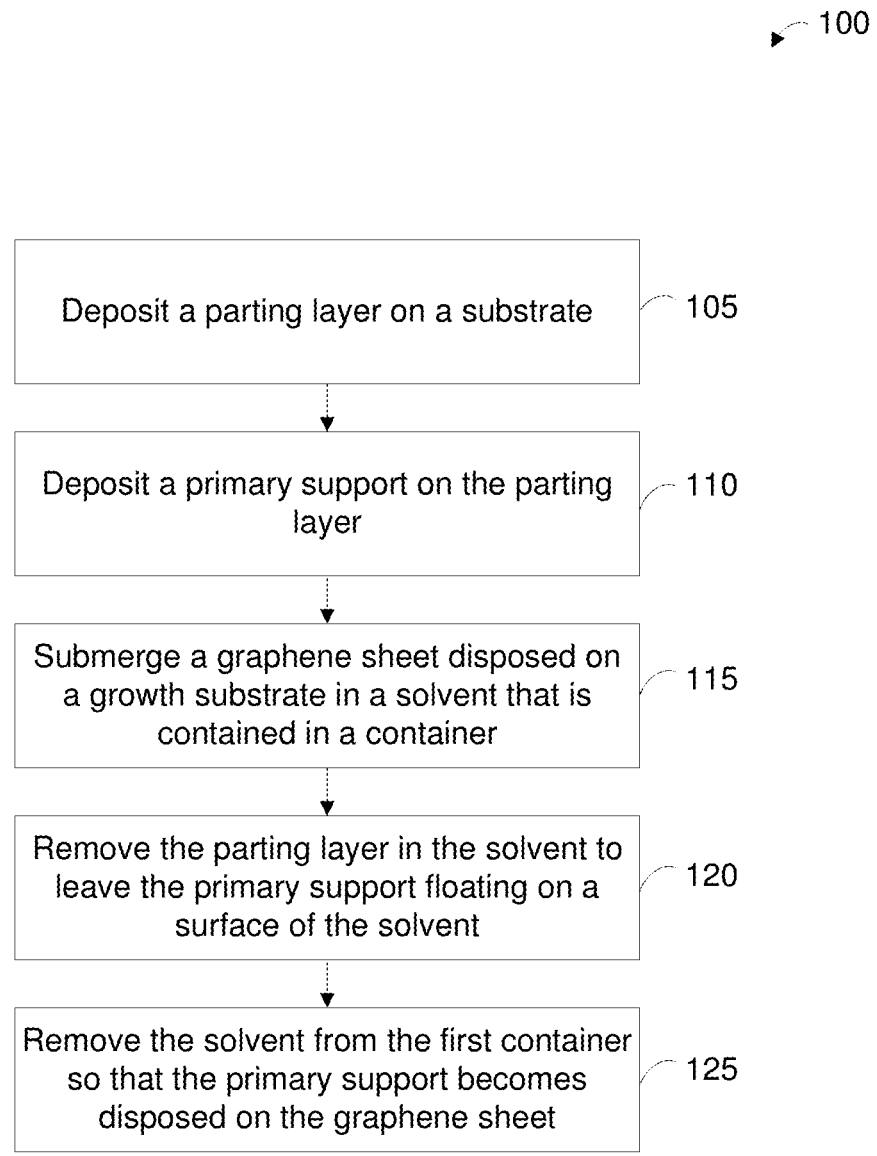
FIG. 1 shows an example of a flow diagram illustrating a process for transferring a primary support from a substrate to a graphene sheet.
Figure 2A:
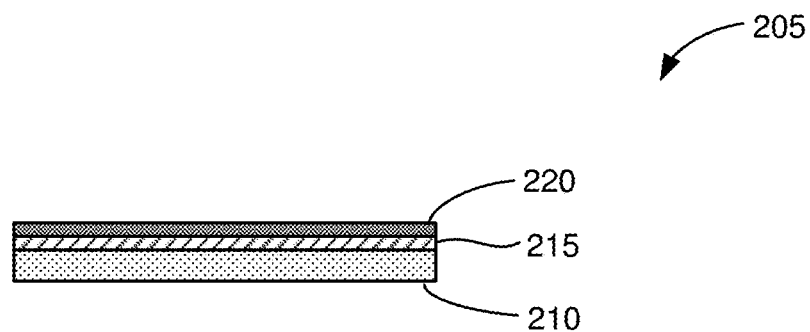
FIGS. 2A-2C show examples of schematic illustrations of operations in a process for transferring a primary support from a substrate to a graphene sheet.
Figure 2B:
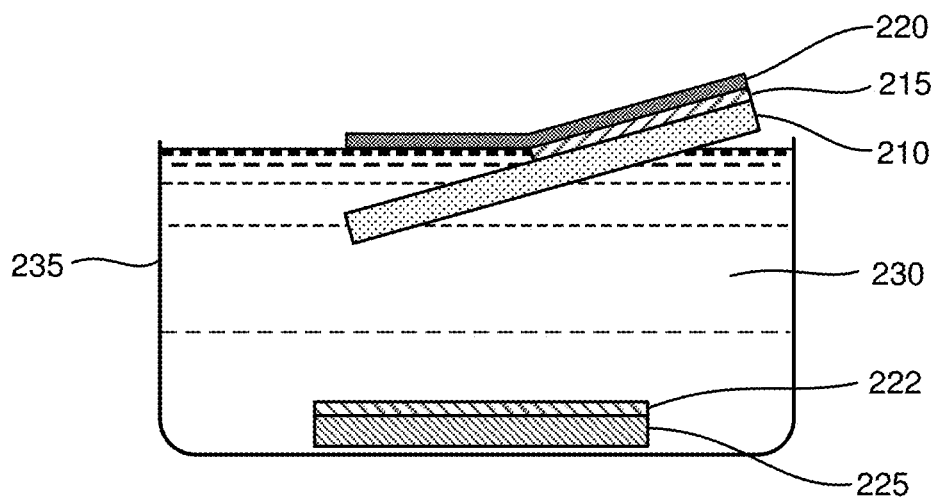
Figure 2C:
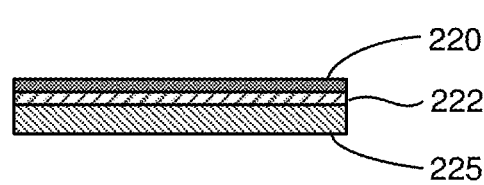

FIG. 1 shows an example of a flow diagram illustrating a process for transferring a primary support from a substrate to a graphene sheet. FIGS. 2A-2C show examples of schematic illustrations of operations in a process for transferring a primary support from a substrate to a graphene sheet. In some embodiments, the graphene sheet is disposed on the substrate on which it was grown (i.e., the growth substrate).

Starting at block 105 of the process 100, a parting layer is deposited on a patterned substrate. In some embodiments, the patterned substrate comprises a patterned silicon substrate. In some embodiments, the patterned substrate comprises a patterned sheet of polycarbonate (e.g., a Nuclepore filter, GE Healthcare Life Sciences, Pittsburgh, Pa.). In some embodiments, the substrate is patterned with depressions (also referred to as trenches) in a surface of the substrate. For example, the substrate may define a grid with a repeat distance, or pitch, of about 1 micron to 2 microns, or about 1 micron, of depressions. In some embodiments, the depression are about 1 micron to 2 microns, about 1 micron, or about 2 microns, diameter circular depressions. In some embodiments, the patterned substrate defines a random pattern of holes. The patterned substrate defines the pattern of openings in the primary support in operation 110. In some embodiments, the parting layer is evaporated onto the patterned substrate.

In some embodiments, the parting layer comprises a water-soluble material. In some embodiments, the parting layer comprises sodium metaphosphate (e.g., Victawet from ICL Industrial Products, Houston, Tex.). In some embodiments, the parting layer comprises lipids. At block 110 of the process 100, a primary support is deposited on the parting layer. In some embodiments, the primary support is evaporated onto the primary support. In some embodiments, the primary support is deposited on the parting layer by spin-coating. In some embodiments, the primary support is deposited on the parting layer by stamping. In some embodiments, the primary support comprises gold, carbon, or a polymer. In some embodiments, the primary support comprises a sheet of polymer with holes defined therein (i.e., a holey polymer film). In some embodiments, the primary support comprises a sheet of gold with holes defined therein (i.e., a holey gold film). For example, the primary support may comprise gold that is evaporated onto the parting layer. In some embodiments, the gold is about 20 nanometers (nm) to 50 nm thick. The material used for the primary support reproduces the pattern of the substrate when the primary support is deposited on the parting layer.

In some embodiments, the primary support comprises a holey carbon film. Holey carbon films are often used for high-resolution studies in conjunction with cryo-electron microscopy. A holey carbon film differs from a continuous carbon film in that a holey carbon film has holes defined in the carbon film. In some embodiments, the holes in the holey carbon film have a specified size. In some embodiments, the holes in the holey carbon film have a dimension of about 1 micron, about 2 microns, or about 1 micron to 2 microns. For example, when the holes in the holey carbon film are circular, the holes have a diameter of about 1 micron, about 2 microns, or about 1 micron to 2 microns. In some embodiments, the center-to-center distance between holes is about 2 microns to 6 microns, about 2 microns to 4 microns, about 4 microns to 6 microns, or about 4 microns. In some embodiments, the holey carbon film has a thickness of about 10 nm to 25 nm, or about 12 nm. Primary supports comprising other materials (i.e., not holey carbon) may be fabricated having the same patterns of holes as described above.

FIG. 2A shows an example of a schematic illustration of the structure formed after block 110 in the process 100. A shown in FIG. 2A, the structure 205 comprises a patterned substrate 210, a parting layer 215 disposed thereon, and a primary support 220 disposed on the parting layer 215.

At block 115 of the process 100, a graphene sheet disposed on a growth substrate is submerged in a solvent that is contained in a container. In some embodiments, the solvent comprises or consists of water or distilled water.

One way in which to produce a graphene sheet is to grow the graphene sheet on a growth substrate. In some embodiments, the growth substrate comprises a copper foil. In some embodiments, the copper foil has a thickness of about 20 microns to 70 microns, or about 45 microns. In some embodiments, an area of the graphene sheet is about 1 centimeter (cm) by 1 cm to about 3 cm by 3 cm, or about 2 cm by 2 cm. In some embodiments, the graphene sheet comprises or consists of a single layer of graphene. In some embodiments, the graphene sheet comprises multiple layers of graphene (e.g., about 2 to 6 layers of graphene).

At block 120 of the process 100, the parting layer is dissolved or otherwise removed in the solvent to leave the primary support floating on a surface of the solvent. In some embodiments, dissolving or otherwise removing the parting layer takes about 2 minutes to 4 minutes, or about 3 minutes.

FIG. 2B shows an example of the process 100 at block 120. As shown in FIG. 2B, a graphene sheet 222 disposed on a growth substrate 225 is submerged in a solvent 230 contained in a container 235. The parting layer 215 is being dissolved or removed, separating the primary support 220 from the substrate 210. A portion of the primary support 220 is floating on the surface of the solvent 230.

At block 125 of the process 100, the solvent is removed from the container so that the primary support becomes disposed on the graphene sheet. In some embodiments, the solvent is pumped out of the container (e.g., using a peristaltic pump). In some embodiments, the solvent is drained from the container using an outlet in the bottom of the container. In some embodiments, the primary support is positioned or repositioned on the surface of the solvent when the solvent is removed from the container so that the primary support becomes disposed on the graphene sheet.

Figure 5:
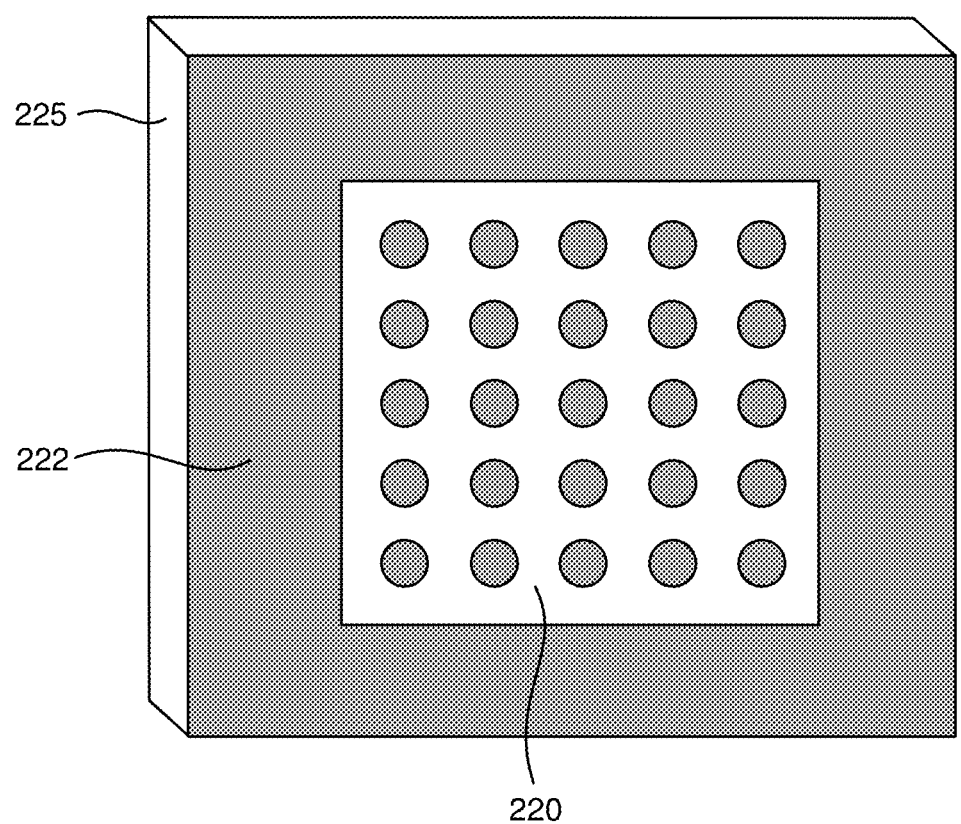
FIG. 5 shows an example of a schematic illustration of a primary support disposed on a graphene sheet.

FIG. 2C shows an example of a schematic illustration of the structure formed after block 125 in the process 100. As shown in FIG. 2C, the structure 240 comprises the graphene sheet 222 disposed on the growth substrate 225, and the primary support 220 disposed on the graphene sheet 222. FIG. 5 shows an example of a schematic illustration of a primary support disposed on a graphene sheet. As shown in FIG. 5, the graphene sheet 222 is disposed on the growth substrate 225, and the primary support 220 is disposed on the graphene sheet 222.

In some embodiments, after block 125, the solvent is removed from the growth substrate, the graphene sheet, and the primary support. For example, the solvent may be allowed to evaporate from the growth substrate, the graphene sheet, and the primary support.

The structure shown in FIG. 2C can be fabricated using other processes. In some embodiments, a graphene sheet disposed on a growth substrate is provided. A pattern of a specified primary support is defined on a surface of a block of material. The pattern is coated with a polymer to be used as a primary support. For example, the polymer could be deposited on the pattern. As another example, the pattern could be dipped into the polymer (e.g., the polymer being a liquid). The pattern with the polymer disposed thereon is then contacted with the graphene sheet, leaving the polymer forming the primary support disposed on the graphene sheet. The polymer is then cured or polymerized (e.g., with ultraviolet light or with a chemical method).

Figure 3:
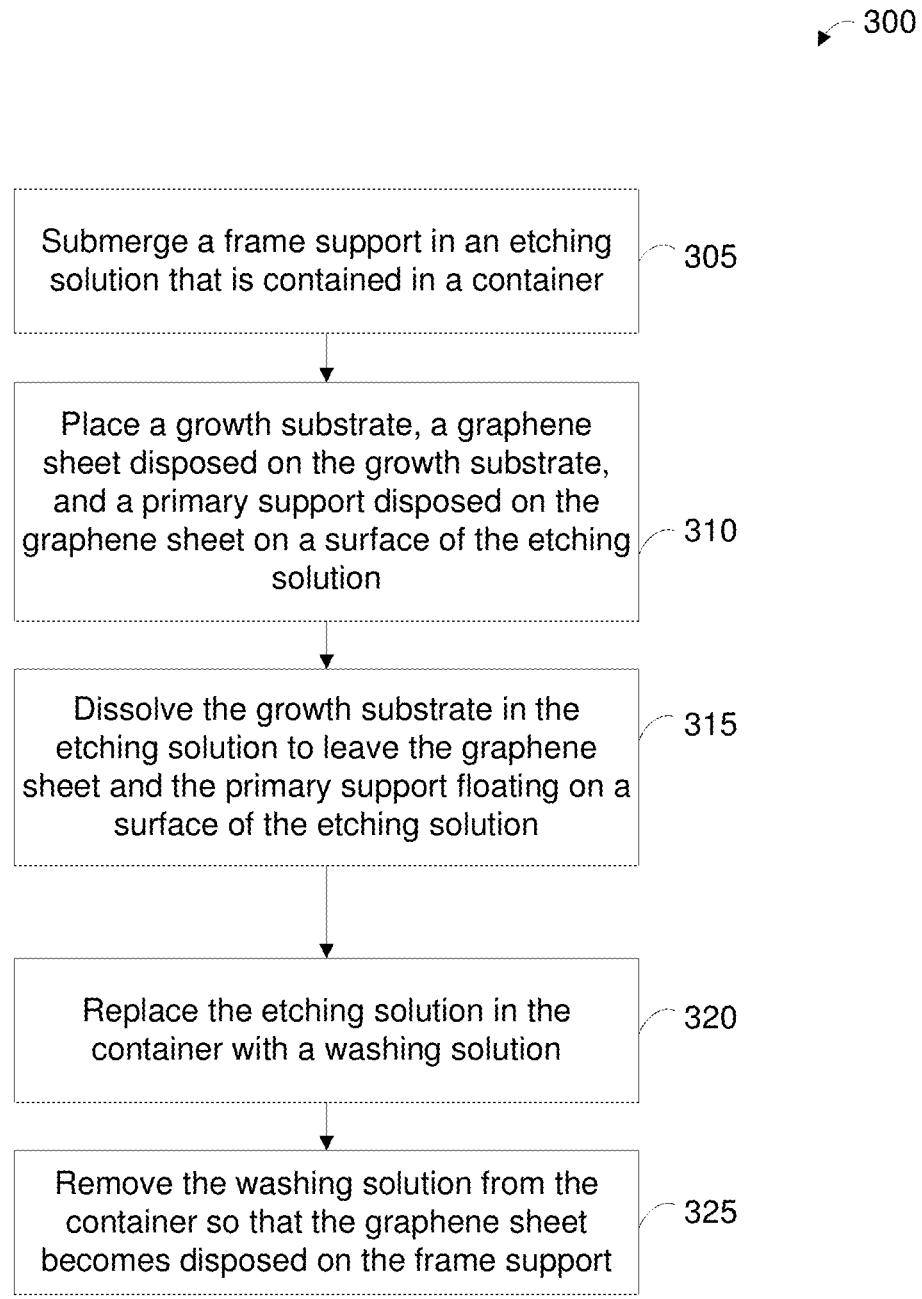
FIG. 3 shows an example of a flow diagram illustrating a process for transferring a graphene sheet from a growth substrate to a frame support.
Figure 4A:
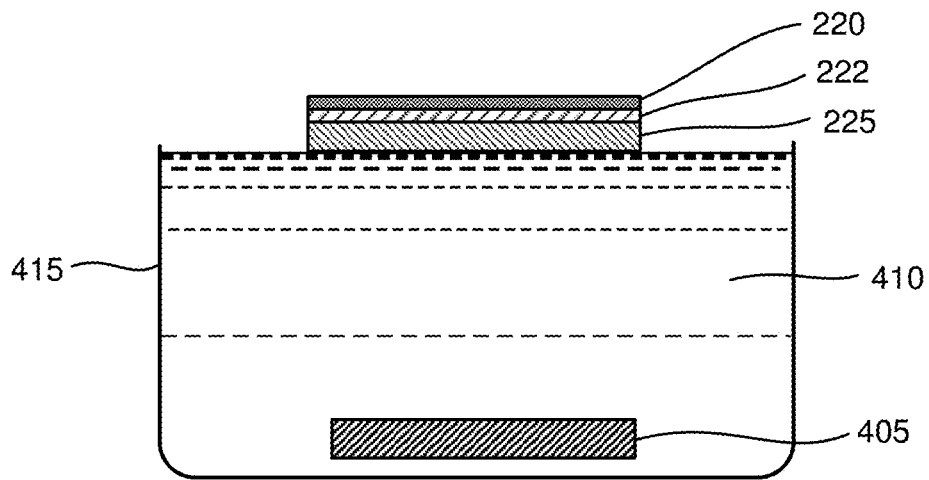
FIGS. 4A-4C show examples of schematic illustrations of operations in a process for transferring a graphene sheet from a growth substrate to a frame support.
Figure 4B:
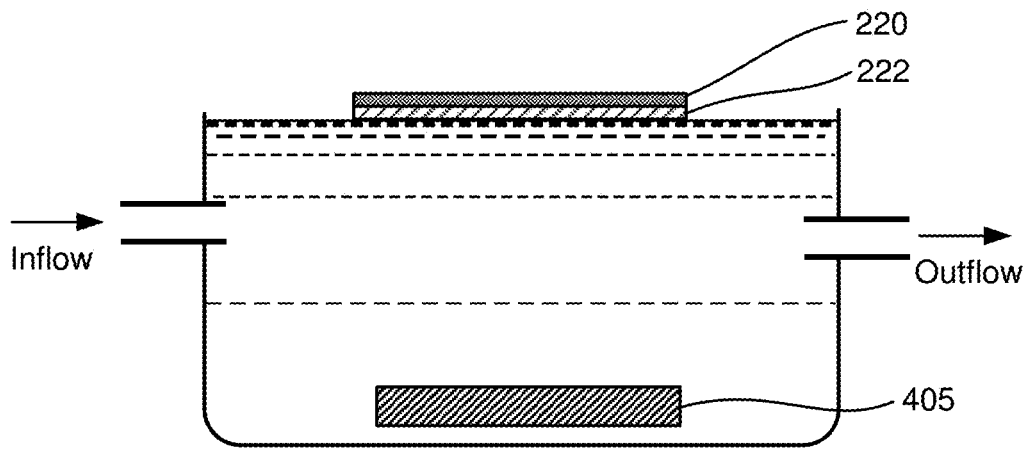
Figure 4C:
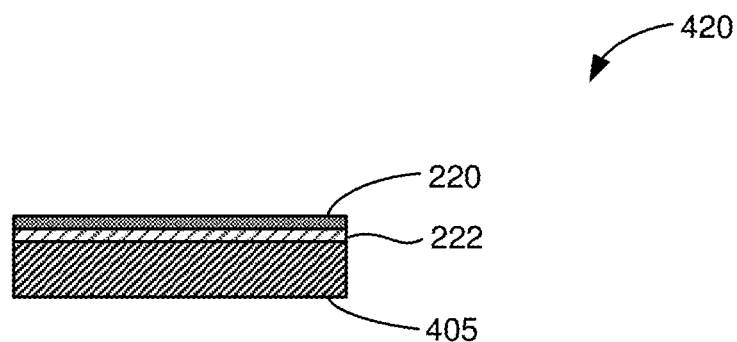

FIG. 3 shows an example of a flow diagram illustrating a process for transferring a graphene sheet from a growth substrate to a frame support. In some embodiments, the graphene sheet has a primary support disposed thereon when it is transferred from the growth substrate to the frame support. FIGS. 4A-4C show examples of schematic illustrations of operations in a process for transferring a graphene sheet from a growth substrate to a frame support.

Starting at block 305 of the process 300 shown in FIG. 3, a frame support is submerged in an etching solution that is contained in a container. In some embodiments, the same container is used for both the process 100 shown in FIG. 1 and the process 300 shown in FIG. 3.

In some embodiments, the frame support comprises an electron microscopy grid. In some embodiments, the frame support consists of an electron microscopy grid. An electron microscopy grid is a grid upon which a sample to be observed in an electron microscope can be placed. The electron microscopy grid can be placed in an electron microscopy specimen holder that can be inserted into the electron microscope. Electron microscopy grids are generally used in transmission electron microscopy (TEM).

An electron microscopy grid can be made of a number of materials or a combination or alloy of such materials. In some embodiments, the electron microscopy grid comprises gold, molybdenum, titanium, or copper. It is believed that molybdenum has a thermal expansion that is matched with carbon, which may be desirable in some cases. An electron microscopy grid is generally an about 3.05 mm diameter disc that has a thickness of about 30 microns and a mesh size of about 100 microns. In some embodiments, an electron microscopy grid has a thickness of about 30 microns and a mesh size of about 100 microns. In some embodiments, the electron microscopy grid defines a grid of open squares, which each of the squares being about 50 microns by 50 microns. In some embodiments, each of the squares is about 50 microns from other squares (i.e., there is about 50 microns of grid material between each of the squares).

These openings in an electron microscopy grid are generally too large for a single layer of graphene to be self-supported over the openings. One method to overcome this problem includes placing a primary support (i.e., a film to support the graphene, which may be a holey carbon film with circular openings having diameters of about 1 micron) on the electron microscopy grid. The graphene sheet can then be transferred onto the primary support. Embodiments described herein are different compared to this method. Embodiments described herein include methods of transferring a primary support (e.g., a holey support, such as a holey carbon film) onto a graphene sheet while the graphene sheet is disposed on its growth substrate (e.g., a copper film). The growth substrate is then dissolved, and the graphene with the primary support disposed thereon is deposited on a frame support (e.g., an electron microscopy grid).

Figure 6A:
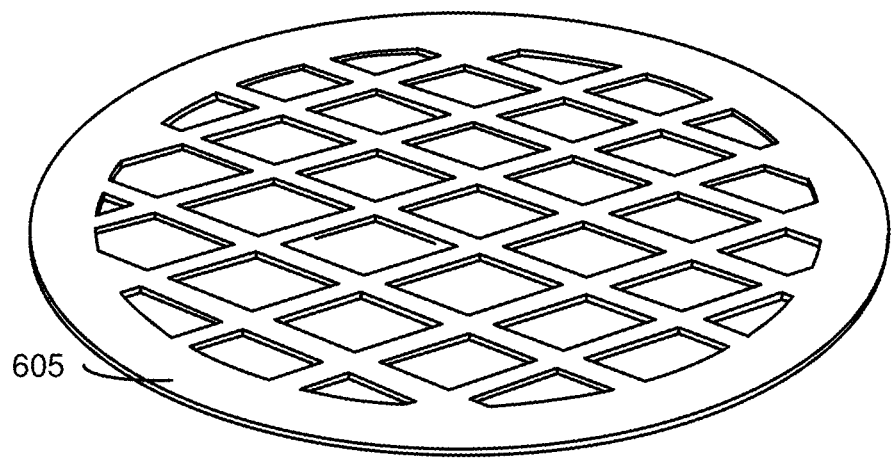
FIGS. 6A and 6B show examples of schematic illustrations of electron microscopy grids.
Figure 6B:
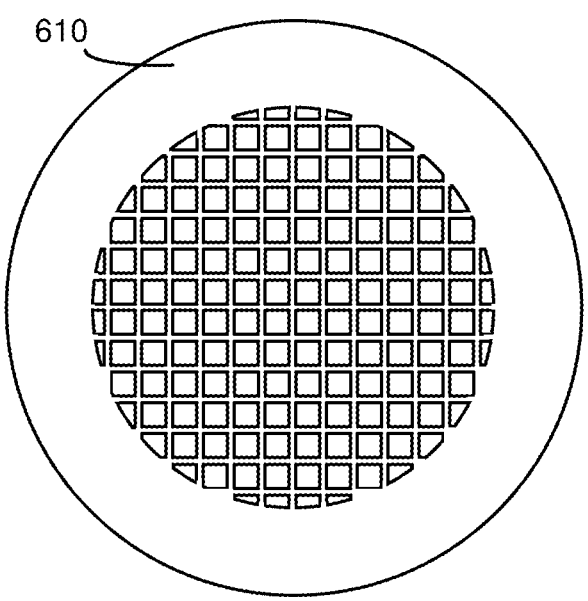

In some embodiments, the electron microscopy grid does not have any other materials disposed thereon. For example, in some embodiments, the electron microscopy grid does not have a holey carbon film disposed thereon. FIGS. 6A and 6B show examples of schematic illustrations of electron microscopy grids. FIG. 6A shows an example of a schematic illustration of an electron microscopy grid 605. FIG. 6B shows an example of a top-down view of an electron microscopy grid 610.

A purpose of the etching solution is to dissolve the growth substrate on which the graphene is disposed. Generally, graphene is grown on a growth substrate comprising a copper foil. In some embodiments, the etching solution comprises a copper etching solution. In some embodiments the etching solution comprises ammonium persulfate dissolved in water or distilled water.

At block 310 of the process 300, a growth substrate, a graphene sheet disposed on the growth substrate, and a primary support disposed on the graphene sheet is placed on a surface of the etching solution. The growth substrate, the graphene sheet, and the primary support float on the surface of the etching solution because of the surface tension of the etching solution. When the growth substrate is placed on the surface of the etching solution, the etching solution begins dissolving the growth substrate.

FIG. 4A shows an example of the process 300 at block 310. As shown in FIG. 4A, a frame support 405 is submerged in an etching solution 410 contained in a container 415. The growth substrate 225 is being dissolved in the etching solution 410.

At block 315 of the process 300, the growth substrate is dissolved in the etching solution to leave the graphene sheet and the primary support floating on a surface of the etching solution. In some embodiments, it takes a period of about 2 hours to 4 hours or about 2 hours to 3 hours to dissolve the growth substrate.

At block 320 of the process 300, the etching solution in the container is replaced with a washing solution. In some embodiments, the washing solution is flowed into one side of the container and the etching solution (and eventually the washing solution after the etching solution is removed from the container) is drained from another side of the container. In some embodiments, the etching solution is pumped out of the container (e.g., using a peristaltic pump) while at the same time the washing solution is flowed into the container. In some embodiments, the etching solution is drained from the container using an outlet in the bottom of the container while at the same time the washing solution is flowed into the container. In some embodiments, the washing solution comprises or consists of water or distilled water.

FIG. 4B shows an example of the process 300 at block 320. As shown in FIG. 4B, the graphene sheet 222 with the primary support 220 disposed thereon is floating on a surface of the etching solution 410 that is being replaced with the washing solution.

At block 325 of the process 300, the washing solution is removed from the container so that the graphene sheet becomes disposed on the frame support. In some embodiments, the washing solution is pumped out of the container (e.g., using a peristaltic pump). In some embodiments, the washing solution is drained from the container using an outlet in the bottom of the container. In some embodiments, the graphene sheet with the primary support disposed thereon is positioned or repositioned on the surface of the washing solution when the washing solution is removed from the container so that the graphene sheet becomes disposed on the frame support.

In some embodiments, an alcohol (e.g., isopropyl alcohol) is added to the washing solution when the graphene is proximate the frame support. The alcohol can aid in orienting the graphene sheet so that it is disposed on the frame support when the washing solution is being removed from the container. The graphene sheet may move away from the frame support when it becomes close to the frame support due to the graphene sheet being hydrophobic and the frame support being easily wetted.

FIG. 4C shows an example of a schematic illustration of the structure formed after block 325 in the process 300. As shown in FIG. 4C, the structure 420 comprises the primary support 220 disposed on the graphene sheet 222, and the graphene sheet 222 disposed on the frame support 405.

In some embodiments, after block 325, the washing solution is removed from the primary support, the graphene sheet, and the frame support. For example, the washing solution may be allowed to evaporate from the primary support, the graphene sheet, and the frame support.

CONCLUSION

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A method comprising:
   (a) submerging a frame support in an etching solution that is contained in a container;
   (b) placing a growth substrate, a graphene sheet disposed on the growth substrate, and a primary support disposed on the graphene sheet on a surface of the etching solution;
   (c) dissolving the growth substrate in the etching solution to leave the graphene sheet and the primary support floating on a surface of the etching solution;
   (d) replacing the etching solution in the container with a washing solution; and
   (e) removing the washing solution from the container so that the graphene sheet becomes disposed on the frame support.

2. The method of claim 1, wherein the frame support comprises an electron microscopy grid.

3. The method of claim 1, wherein the frame support comprises an electron microscopy grid, and wherein no other materials are disposed on the electron microscopy grid.

4. The method of claim 1, wherein the growth substrate comprises a copper foil.

5. The method of claim 1, wherein the graphene sheet comprises a single layer of graphene.

6. The method of claim 1, wherein the graphene sheet comprises a multiple layers of graphene.

7. The method of claim 1, wherein the primary support comprises a holey carbon film.

8. The method of claim 1, wherein the primary support comprises a sheet of gold with holes defined therein.

9. The method of claim 1, wherein the etching solution comprises a copper etching solution.

10. The method of claim 1, wherein the etching solution comprises ammonium persulfate dissolved in water.

11. The method of claim 1, further comprising:
    adding an alcohol to the washing solution during operation (e).

12. The method of claim 11, wherein the alcohol comprises isopropyl alcohol.

13. The method of claim 1, wherein the washing solution comprises water.

14. The method of claim 1, further comprising:
    after operation (e), removing the washing solution from the frame support, the graphene sheet, and the primary support.

15. A method comprising:
    (a) submerging a frame support in an etching solution that is contained in a container, the etching solution comprising a copper etching solution;
    (b) placing a growth substrate, a graphene sheet disposed on the growth substrate, and a primary support disposed on the graphene sheet on a surface of the etching solution, the growth substrate comprising a copper foil;
    (c) dissolving the growth substrate in the etching solution to leave the graphene sheet and the primary support floating on a surface of the etching solution;
    (d) replacing the etching solution in the container with a washing solution, the washing solution comprising water; and
    (e) removing the washing solution from the container so that the graphene sheet becomes disposed on the frame support.

16. The method of claim 15, further comprising:
    adding an alcohol to the washing solution during operation (e).

17. The method of claim 15, wherein the frame support comprises an electron microscopy grid.

18. The method of claim 15, wherein the graphene sheet comprises a single layer of graphene.

19. The method of claim 15, wherein the primary support comprises a holey carbon film.

* * * * *